United States Patent [19]
Lutz et al.

[11] Patent Number: 6,143,204
[45] Date of Patent: Nov. 7, 2000

[54] STABILIZATION OF IODOPROPYNL COMPOUNDS

[75] Inventors: Patrick Jay Lutz, Nazareth; Susan Alcorn Ban, Kunkletown, both of Pa.; Thomas Edward Farina, Flemington, N.J.

[73] Assignee: Lonza Inc., Fair Lawn, N.J.

[21] Appl. No.: 09/099,726

[22] Filed: Jun. 19, 1998

[51] Int. Cl.[7] .................. C09K 3/00; A61L 9/01; A01N 2/08; A01N 43/50

[52] U.S. Cl. .................. 252/384; 422/28; 424/76.8; 514/389

[58] Field of Search .................. 252/384; 422/28; 424/76.8; 514/389

[56] References Cited

U.S. PATENT DOCUMENTS

| | | | |
|---|---|---|---|
| 3,987,184 | 10/1976 | Foelsch | 514/389 |
| 4,163,797 | 8/1979 | Burk et al. | 514/528 |
| 4,172,140 | 10/1979 | Shull et al. | 514/389 |
| 4,844,891 | 7/1989 | Rosen et al. | 424/76.4 |
| 5,073,570 | 12/1991 | Tseng | 514/533 |
| 5,346,913 | 9/1994 | Hsu et al. | 514/389 |
| 5,405,862 | 4/1995 | Farina et al. | 514/389 |
| 5,428,050 | 6/1995 | Merianos | 514/390 |
| 5,496,842 | 3/1996 | Merianos | 514/389 |
| 5,552,425 | 9/1996 | Merianos | 514/390 |
| 5,631,273 | 5/1997 | Merianos | 514/389 |
| 5,840,323 | 11/1998 | Taha et al. | 424/405 |
| 5,886,031 | 3/1999 | Shin et al. | 514/478 |

FOREIGN PATENT DOCUMENTS

| | | | |
|---|---|---|---|
| 0 327 220 | 8/1989 | European Pat. Off. | A01N 47/36 |
| 0 571 903 | 5/1993 | European Pat. Off. | C07D 233/78 |
| WO 95/29588 | 11/1995 | WIPO | A01N 37/12 |
| WO 96/39836 | 12/1996 | WIPO | A01N 47/12 |

OTHER PUBLICATIONS

Derwent Publications Ltd, JP 10 158110, 1998.

Primary Examiner—Jill Warden
Assistant Examiner—LaToya Cross
Attorney, Agent, or Firm—Darby & Darby

[57] ABSTRACT

A highly stable liquid formulation having broad spectrum preservative properties which constitutes an admixture of a dialkanol-substituted DMH, an iodopropynyl compound, a stabilizer of a hydantoin, urea or derivative thereof, and a hydroxyl solvent. Preferably the constituents are dimethyloldimethylhydantoin, 3-iodo-2-propynylbutyl carbamate, dimethylhydantoin, and a glycol solvent. The preservative preferably has a total formaldehyde content of 5% and less than 0.2% of free formaldehyde. The composition is prepared by successively admixing the dialkanol-substituted dimethylhydantoin and the stabilizer, the hydroxyl solvent, and the iodopropynyl compound. Also described is a stabilized iodopropynyl compound preferably containing dimethylhydantoin as the stabilizer.

6 Claims, 2 Drawing Sheets

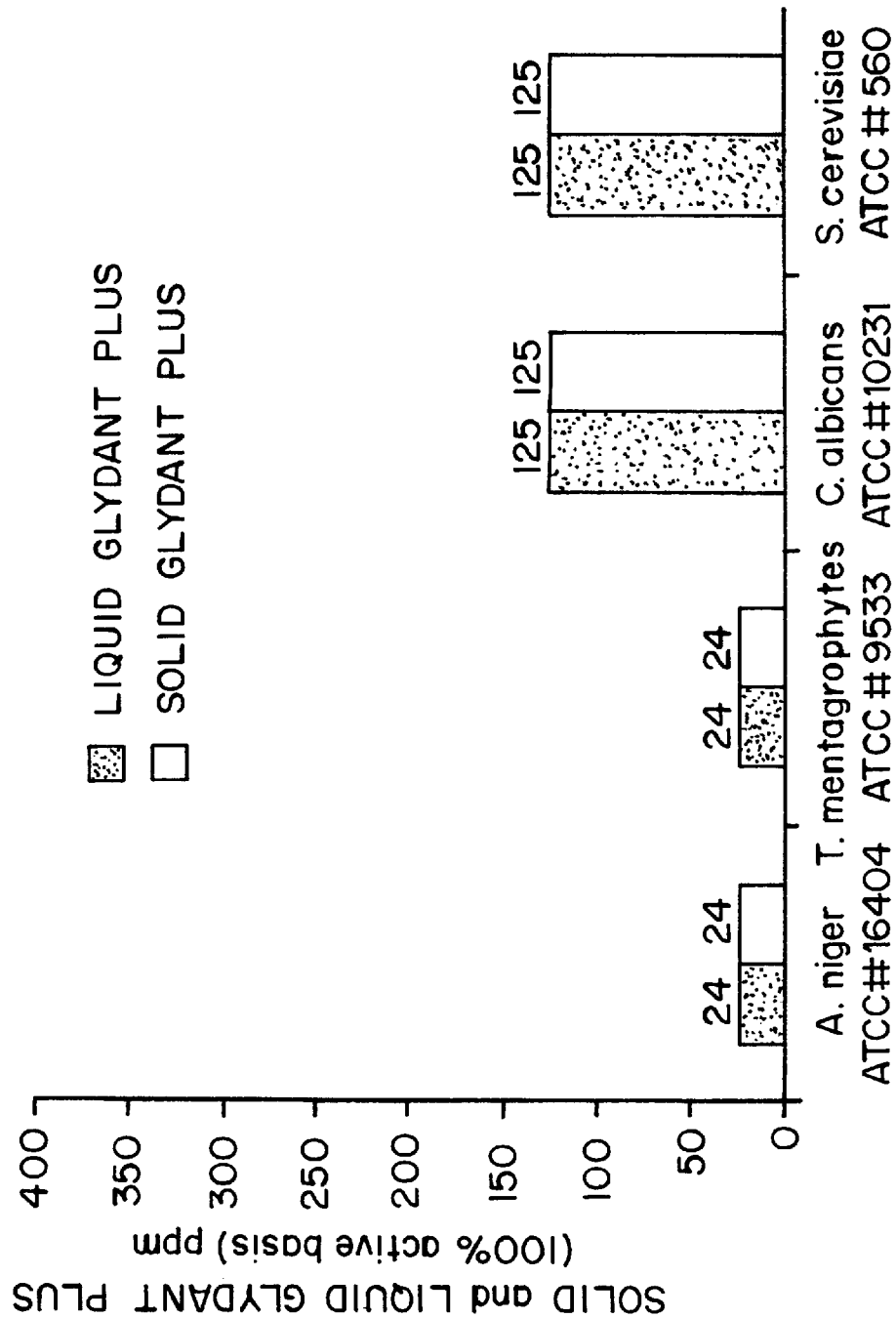

STABILIZATION OF IODOPROPYNL COMPOUNDS

BACKGROUND OF THE INVENTION

The need for effective and economical preservative compositions is well known. There are a wide variety of applications where inhibiting the growth of microorganisms is necessary, as for example personal care products such as shampoos, creams, lotions, cosmetics, soap and household products such as laundry detergents, hard surface cleaners, and fabric softeners. The shelf life of these preparations depends on their resistance to microbial spoilage.

In addition, in many industrial applications, antimicrobial agents are useful in paint, wood, textiles, adhesives, sealants, leather, rope, paper pulp, plastics, fuel, oil, and rubber and metal working fluids. The control of slime-producing bacteria and fungi in pulp and paper mills and cooling towers is a matter of substantial commercial importance.

For the foregoing applications the demand for stable broad-spectrum preservatives has increased. In recent years, these needs have been met with solid formulations. For example, combinations of formaldehyde donors (e.g., dimethyloldimethylhydantoin (DMDMH)) and halopropynyl compounds (e.g., 3-iodo-2-propynylbutyl carbamate (IPBC)) have achieved considerable commercial success. Such synergistic combinations have been described in U.S. Pat. No. 4,844,891.

Furthermore, because of the demand of governmental regulations, low free-formaldehyde products are needed. Research in this area has also proved beneficial. For example, in the case of DMDMH, improved formulation and processing has resulted in compositions which contain less than 0.1% free formaldehyde. (See U.S. Pat. No. 5,405,862.) In contrast, earlier formulations of DMDMH had over 1% of free formaldehyde. (See U.S. Pat. No. 3,987,184.)

At the present time, in addition to meeting the above criteria, the industry is demanding liquid forms of preservatives as the use of automatic liquid blending systems becomes more popular. Unfortunately, preservatives that are in liquid form, highly stable, broad spectrum, and low in free formaldehyde have eluded formulators.

SUMMARY OF THE INVENTION

It has now been discovered that highly stable, liquid formulations of broad spectrum preservatives can be prepared by admixing alkanol-substituted dimethylhydantoins, iodopropynyl compounds, stabilizers, and a solvent. This invention is based, in part, on the unexpected finding that the iodopropynyl compounds can be stabilized at high temperatures by the addition of hydantoin-type stabilizers such as dimethylhydantoin. Furthermore, the compositions of the invention have surprisingly good physical stability at low temperatures and enhanced solubility which allows the easy preparation of these highly concentrated mixtures. Such highly concentrated preservatives useful in automatic liquid blending systems could not heretofore be prepared.

BRIEF DESCRIPTION OF THE FIGURES

FIG. 2 illustrates the results of a 72 hour minimum inhibitory concentration test against 4 fungal organisms of the liquid formulation of the invention and a solid formulation of DMDMH and IPBC.

DETAILED DESCRIPTION OF THE INVENTION

Figure 1:
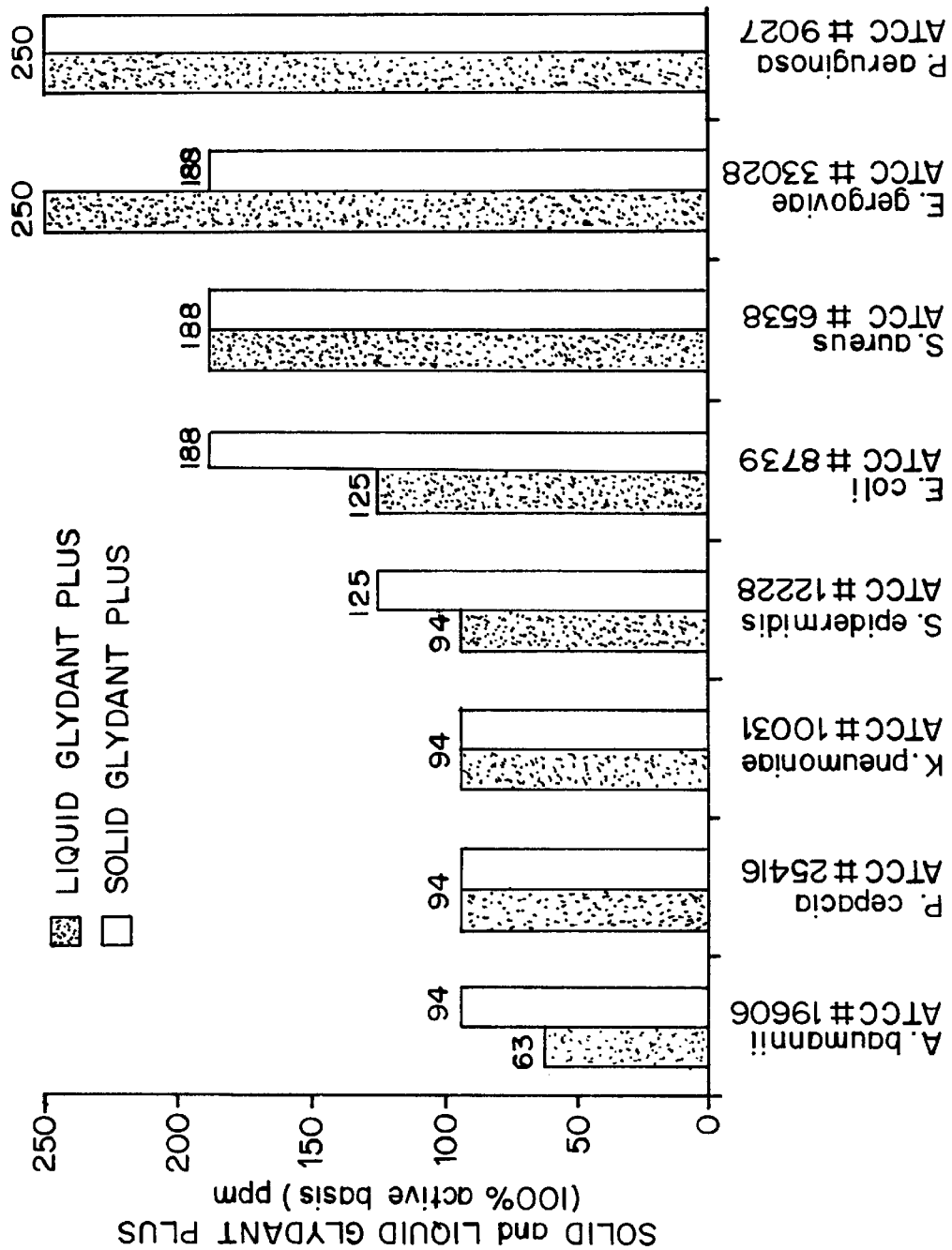
FIG. 1 illustrates the results of a 48 hour minimum inhibitory concentration test against 8 bacteria organisms of the liquid formulation of the invention and a solid formulation of DMDMH and IPBC.

|  | Broad wt. % | Preferred wt. % |
| --- | --- | --- |
| Dialkanol-substituted DMH | 20–95 % | 75–85 % |
| Iodopropynyl Compound | 0.2–20 | 1–5 |
| Stabilizer | 1–30 | 5–20 |
| Hydroxyl Solvent | 0–60 | 2–20 |

The ratio of the stabilizer to the iodopropynyl compound may broadly be from about 150:1 to 0.05:1, preferably from 20:1 to 1:1, most desirably from about 10:1 to 2:1.

The alkanol-substituted DMH compounds used in the invention are well known and include those defined in U.S. Pat. Nos. 3,987,184 and 4,172,140, the entire contents of which are incorporated herein by reference. These are condensation products of 5,5-dimethylhydantoin with 1, 2, or more moles of formaldehyde (e.g., 1,3-dimethylol-5,5-dimethylhydantoin, 1-methylol-5,5-dimethylhydantoin, 3-methylol-5,5-dimethylhydantoin, 1,3-dimethyloloxymethylene-5,5-dimethylhydantoin, 1-methylol-3-methyloloxymethylene-5,5-dimethylhydantoin, and mixtures thereof).

Examples of compounds which may be used as the iodopropynyl component of the invention are the fungicidally active iodopropynyl derivatives. These include compounds derived from propynyl or iodopropynyl alcohols such as the esters, ethers, acetals, carbamates and carbonates and the iodopropynyl derivatives of pyrimidines, triazolinones, tetrazoles, triazinones, sulfamides, benzothiazoles, ammonium salts, carboxamides, hydroxamates, and ureas. Preferred among these compounds is 3-iodo-2-propynylbutyl carbamate, IPBC. These compounds are included within the broadly useful class of compounds having the generic formulas such as I and II shown below:

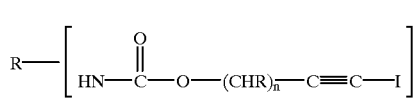

wherein:
R is selected from the group consisting of substituted and unsubstituted alkyl, aryl, and alkylaryl groups having from 1 to 20 carbon atoms; and
m and n are independent integers from 1 to 3.

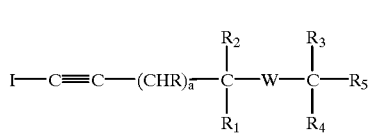

wherein:
$R_1$ and $R_2$ are defined as $R_3$ and $R_4$ below or are joined to form a cycloalkyl, cycloalkenyl, aromatic or a heterocyclic ring containing an oxygen, nitrogen or sulfur atom or an alkoxy, amino, carbonyl, carboxyl, halo, hydroxyl, keto or a thiocarboxyl-substituted derivative thereof;

$R_3$, $R_4$ and $R_5$ are independently selected from (A) hydrogen, alkyl, cycloalkyl, alkenyl, cycloalkenyl, aryl, a heterocyclic ring containing an oxygen, nitrogen or sulfur atom, alkoxy, amino, carbonyl, carboxyl, halo, hydroxyl, keto or a thiocarboxyl and (B) substituted derivatives of the alkyl, cycloalkyl, alkenyl, cycloalkenyl, aryl and the heterocyclic ring wherein the substitutions are alkyl, cycloalkyl, alkenyl, cycloalkenyl, aryl, alkoxy, amino, carboxyl, halo, hydroxyl, keto or a thiocarboxyl;

a is 0 to 16;

W may be a single bond, oxygen, $NR_6$, or $(CR_7R_8)_m$, wherein $R_6$ is hydrogen, alkyl, cycloalkyl, alkenyl, cycloalkenyl, aryl or a heterocyclic ring containing an oxygen, nitrogen or sulfur atom or a substituted derivative of alkyl, cycloalkyl, alkenyl, cycloalkenyl or aryl groups wherein the substitutions are alkyl, cycloalkyl, alkenyl, cycloalkenyl, aryl, alkoxy, amino, carbonyl, carboxyl, halo, hydroxyl, keto, or a thiocarboxyl wherein $R_6$, $R_7$ and $R_8$ are defined as $R_3$ and $R_4$ above and m is an integer from 1 to 12. The above definition of $R_6$ includes, among other things, an aminoalkyl group.

The heterocyclic rings referred to in the above definitions may contain from 5 to 8 members, the alkyl or cycloalkyl groups from 1 to 18 atoms, the alkenyl or cycloalkenyl groups from 2 to 18 carbon atoms, and the aryl groups from 6 to 10 members.

In formula II, when $R_1$ and $R_2$ are hydrogen, $R_3$ and $R_4$ are carbonyl, $R_5$ is —CH=CH—$CO_2H$; a is equal to 0; and W is oxygen, the compound is iodopropynyl maleate,

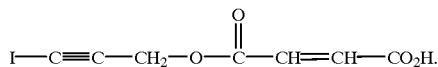

Other compounds include the mono-iodopropynyl esters of anhydrides such as succinic and phthalic as well as the following anhydrides: ethylenediamine tetraacetic dianhydride, 3,3-dimethylglutaric anhydride, S-acetylmercaptosuccinic anhydride, dichloromaleic anhydride, 2-dodecen-1-yl succinic anhydride and cis-5-norbornene-endo-2,3-dicarboxylic anhydride. Where hydrophilicity is desired, the sodium salts may be used because of their extremely high water solubility. Preferred carboxylic acid anhydrides include succinic, itaconic, phthalic, tetrachlorophthalic, and diglycolic anhydride. Such compounds are defined in U.S. Pat. Nos. 4,844,891 and 5,073,570.

The stabilizers used in the invention are hydantoin and urea and their derivatives, most preferably 5,5-dimethylhydantoin.

Hydantoins and their derivatives may be represented by formulas III, IV, and V:

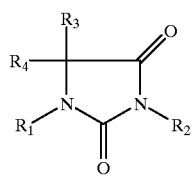

where $R_1$ to $R_4$ are independently selected from H, $C_1$ to $C_{22}$.

N,N"-Methylenebis[N'-2,5-dioxo-4-imidazolidinyl]urea and its derivatives:

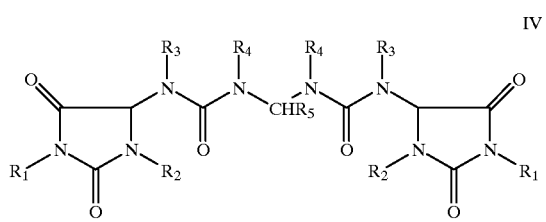

where $R_1$ to $R_5$ are independently selected from H or $C_1$ to $C_{22}$.

2,5-Dioxo-4-imidazolidinyl urea (5-ureidohydantoin) and its derivatives:

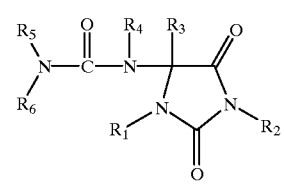

wherein $R_1$ to $R_3$ are independently selected from H, $CH_3$, $C_2H_5$ or $C_3H_7$.

Urea and its derivatives are represented by Formula VI:

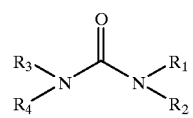

where $R_1$ to $R_4$ are independently selected from H or $C_1$ to $C_{12}$. Where all the R groups are H, the compound is urea.

The solvents which may be used in the invention include mono-, di-, and polyhydroxyl alcohols. For example, monohydroxyl alcohols having from about 1 to 5 carbon atoms, most preferably ethanol and propanol, may be used. Dihydroxyl alcohols (i.e., glycols) such as $C_2$ to $C_8$ diols such as propylene glycol and butylene glycol are advantageous. 1,3-Butylene glycol is particularly preferred. Other compounds which can be used include: dipropylene glycol, glycerin, diglycerin, PPG-9, PPG-2-buteth-2, butoxypropanol, butoxydiglycol, PPG-2 butyl ether, glycereth-7, sorbitol, isopentyldiol, myristyl myristate, and phenoxy ethanol.

The preservative formulations of the instant invention can be readily prepared in accordance with procedures well known to those skilled in the art. The preferred procedure is first to mix the stabilizer at temperatures ranging from 30° C. to 50° C. with the dialkanol-substituted dimethylhydantoin. This mixture is stirred for 5 minutes at 30° C. It may be heated to 50° C. to increase the solution rate. Thereafter the hydroxylic solvent is added and the entire mixture is stirred over a period of 5 minutes. Finally, the iodopropynyl compound is added and mixed for another 15 minutes to form a homogeneous solution. The total mixing time is approximately 30 minutes.

The liquid preservative composition of the invention has a free formaldehyde concentration of less than 1 wt. %, preferably less than 0.2. The total formaldehyde concentration is from 5 wt. % to 25 wt. %, and preferably from 12 wt. % to 14 wt. %.

The preservatives of the invention can be used as active compounds for combating microorganisms, in particular for the preservation of cosmetics, personal care products, household products, and industrial materials such as adhesives, sizes, paper and cardboard, textiles, leather, wood, paints and articles made of plastic, cooling lubricants and other materials which can be attacked or decomposed by microorganisms. Components of production plants, for example cooling water, which can be impaired by multiplication of microorganisms, may also be beneficially treated. Also, the integrity of other water-containing systems, such as swimming pools and spas, can be maintained by use of the preservatives of the invention. In addition, they can be used to control and eliminate microorganisms by disinfection and sanitization of surfaces, such as found in homes, institutions, and hospitals.

Examples of microorganisms which can effect contamination, degradation, or a change in the industrial environments and materials are bacteria, fungi, yeasts, algae, and slime organisms. The active compounds of the invention act against fungi, in particular mold fungi, fungi which discolor and destroy wood (Basidiomycetes), and against slime organisms and algae.

Microorganisms of the following genera are examples: Alternaria, such as *Alternaria tenuis,* Aspergillus, such as *Aspergillus niger,* Chaetomium, such as *Chaetomium globosum,* Candida, such as *Candida albicans,* Lentinus, such as *Lentinus tigrinus,* Penicillium, such as *Penicillium glaucum,* Trichophyton, such as *Trichophyton mentagrophytes,* Aureobasidium, such as *Aureobasidium pullulans,* Enterobacter, such as *Enterobacter gergoviae,* Trichoderma, such as *Trichoderma viride,* Escherichia, such as *Escherichia coli,* Pseudomonas, such as *Pseudomonas aeruginosa* and *Pseudomonas cepacia,* and Staphylococcus, such as *Staphylococcus aureus* and *Staphylococcus epidermidas.*

The use concentrations of the active compounds according to the invention depend on the nature and the occurrence of the microorganisms to be combated, and on the composition of the material to be preserved. The optimum amount to be employed can be determined by means of a series of tests. The use concentrations are in general in the range of 0.00005 (0.5 ppm) to 5% by weight, preferably from 0.0001 to 1%, relative to the material to be preserved.

Liquid compositions of this invention are used directly as they are manufactured without dilution. They may be poured into small batches (from one to thousands of pounds) of product at any point in its manufacture. Also, the liquid compositions may be pumped into medium sized batches (from thousands to tens of thousands of pounds) from a weigh scale.

The preservative of the invention may also be metered continuously from a storage tank into large sized production runs (from tens of thousands to millions of pounds) in systems custom-designed to continuously mix all the components of the finished product at approximately the same rate that it is filled into its final package. The blending elements of continuous mixers are mostly shaped in the form of spirals or screws, effecting on rotation both a mixing and a transport of the product composition.

Because start-up is very labor-intensive, to insure all the metering equipment is properly calibrated, these systems are generally used only for very high volume, long and continuous production runs.

In order to illustrate more fully the subject invention, attention is directed to the following examples:

EXAMPLE 1

A preservative of the instant invention containing 81 parts of Glydant II (a trademark of Lonza Inc.), 12 parts of dimethylhydantoin, 4.5 parts of butylene glycol, and 2.5 parts of iodopropynyl butyl carbamate is described in this example. Glydant II is an aqueous solution containing solids comprising 65% DMDMH, 30% MMDMH, and 5% DMH. It has a total formaldehyde content of 17%.

Initially the DMH and the Glydant II are mixed at 30° C. The mixing continues for 5 minutes during which the temperature is increased to 50° C. Thereafter the butylene glycol is added and stirring is continued for 10 minutes. Finally, the IPBC is added and mixed with the other constituents for 15 minutes to form the final solution. After the mixture is cooled to room temperature, a clear homogeneous liquid solution is obtained. The solution has a total formaldehyde content of 14 wt. %, a free formaldehyde content of 0.05 wt. %, and an IPBC content of 2.3%. After storage for one month at 50° C., the mixture remains a clear, colorless liquid with 92% recovery of the total formaldehyde content and >99% recovery of the IPBC content obtained.

This solution remains clear and colorless even after two months storage at room temperature in sunlight. Significantly, quantitative recovery of total formaldehyde and IPBC is also obtained. Free formaldehyde content is 0.06%.

EXAMPLE 2

To illustrate the suitability of the liquid preservative of the invention for use in automated liquid blending systems, the viscosity and the specific gravity of the formulation described in Example 1 are determined. A Brookfield Model RVT viscometer, Spindle No. 3, at 50 rpm is used to determine viscosity. The following results are obtained:

TABLE 1

| Temperature | Specific Gravity | Viscosity, cps |
| --- | --- | --- |
| 5° C. |  | 120 |
| 15° C. | 1.2043 | — |
| 25° C. | 1.1992 | 40 |
| 30° C. | 1.1960 | — |
| 35° C. | 1.1954 | — |
| 45° C. |  | 30 |
| 65° C. | 1.1625 | 20 |
| 85° C. | 1.1500 | 10 |

The viscosity values and the specific gravity measurements presented in Table 1 for the liquid preservative of this invention are typical of liquids used in automated blending systems. These ideal parameters are dependent on the particular system employed.

EXAMPLE 3

To demonstrate the activity of the liquid preservative described in Example 1, 48 hour minimum inhibitory concentration tests were performed on eight bacteria organisms. These tests compared the liquid preservative of the invention to a solid preservative on a 100% active basis. The composition of the solid preservative was 95% DMDMH and 5% IPBC.

The results obtained from the foregoing tests are set forth in FIG. 1.

It will be noted that the results obtained for the liquid formulation of the invention, as compared to the solid formulation, are substantially comparable. In certain instances the liquid formulation is superior, as in the case of the *A. baumanii,* the *S. epidermidis,* and the *E. coli.* These data show that the liquid formulations of the invention have a broad spectrum activity against a wide range of bacteria.

EXAMPLE 4

Minimum inhibitory concentration tests (72 hours) for the liquid preservative described in Example 1 and the solid preservative defined in Example 3 were performed with respect to four fungal organisms. The comparison was made on a 100% active basis.

FIG. 2 illustrates that the liquid preservative of the invention is as efficacious as the solid in all of the tests performed and that these materials have broad spectrum activity against a variety of fungi.

EXAMPLE 5

A series of formulations were prepared to determine the solubility, free formaldehyde concentration, and physical stability of the compositions of the invention as compared to compositions free of dimethylhydantoin. The formulations are shown in Table 2.

TABLE 2

Liquid Glydant Plus Comparison Chart

| Ingredients - % | A 5503-84-1 | B 5503-84-2 | C 5503-90-1 | D 5503-111-1 | E 5503-111-2 | F 5503-115-1 | G 5503-115-2 |
|---|---|---|---|---|---|---|---|
| IPBC (Poly P-100) | 2.50 | 2.50 | 2.50 | 2.50 | 2.50 | 2.50 | 2.50 |
| Glydant II | 74.70 | 72.85 | 74.70 | 81.00 | 81.00 | 81.00 | 81.00 |
| Prop. Glycol | 22.80 | | 12.80 | 4.50 | | 16.50 | 4.50 |
| But. Glycol | | 24.65 | | | 4.50 | | |
| DMH | | | 10.00 | 12.00 | 12.00 | | |
| D1 Water | | | | | | | 12.00 |
| Solubility | OK | OK | OK | OK | OK | | No good-ppt. |
| Physical Solubility | ppt. after 3rd freeze/thaw | OK after 3rd freeze/thaw | OK after 3rd freeze/thaw | OK after 3rd freeze/thaw | OK after 3rd freeze/thaw | ppt. after 3rd freeze/thaw | |
| % Free HCHO - Initial | 0.20 | 0.24 | 0.07 | 0.03 | 0.05 | 0.17 | |
| % Free HCHO - 1 month @ 40° C. | 0.19 | 0.19 | 0.19 | 0.02 | 0.03 | | |
| % Free HCHO - 2 months @ 40° C. | 0.21 | 0.25 | 0.06 | | | | |
| % Free HCHO - 1 month @ 50° C. | 0.24 | 0.23 | 0.11 | 0.05 | 0.05 | | |
| Comments | Unstable & % free HCHO too high | Stable but % free HCHO too high | Stable & good % free HCHO but % total HCHO not high enough | Stable & low % free HCHO & % total HCHO - OK | Stable & low % free HCHO & total HCHO - OK Going with But. Glycol | Unstable and % free HCHO too high | Insoluble |

The above data show that the liquid compositions of the invention, namely, Formulations 90-1, 111-1, and 111-2, had high solubility, good physical stability, and extremely low free formaldehyde as compared to the formulations free of DMH, namely, Formulations 84-1, 84-2, 115-1, and 115-2. Formulations 111-1 and 111-2 are preferred because of the higher total formaldehyde concentration.

EXAMPLE 6

Using the formulations shown in Table 3, liquid preservatives of the invention were tested to determine the free formaldehyde, total formaldehyde, and percent IPBC after one month stability tests at 40° C. and 50° C., respectively. As will be noted, the formulations contained 10, 12, and 15 parts of dimethylhydantoin. Results are set forth in the following table:

TABLE 3

Chemical Stability Results of the Preferred Aqueous Liquid Systems of the Invention

| Formulation | A 5503-109-1 | B 5503-109-2 | C 5503-111-1 | D 5503-111-2 | E 5503-111-3 |
|---|---|---|---|---|---|
| Parts: | | | | | |
| Glydant II | 81 | 81 | 81 | 81 | 81 |
| IPBC | 2.5 | 2.5 | 2.5 | 2.5 | 2.5 |
| Propylene glycol | 6.5 | — | 4.5 | — | 1.5 |
| Butylene glycol | — | 6.5 | — | 4.5 | — |
| DMH | 10 | 10 | 12 | 12 | 15 |

TABLE 3-continued

Chemical Stability Results of the Preferred Aqueous Liquid Systems of the Invention

| Formulation | A 5503-109-1 | B 5503-109-2 | C 5503-111-1 | D 5503-111-2 | E 5503-111-3 |
|---|---|---|---|---|---|
| %FreeHCHO (criterion for Free HCHO is <0.19%) | | | | | |
| Initial | 0.05 | 0.07 | 0.03 | 0.05 | 0.02 |
| 40° C. Stability 1 Month | 0.05 | 0.05 | 0.02 | 0.03 | 0.03 |
| 50° C. Stability 1 month | 0.07 | 0.05 | 0.05 | 0.05 | 0.02 |
| %TotalHCHO (criterion for Total HCHO is 90% recovery) | | | | | |
| Initial | 14.08 | 14.05 | 14.07 | 14.09 | 14.11 |
| 40° C. Stability 1 Month | 13.04 | 13.10 | 12.33 | 13.16 | 13.19 |
| 50° C. Stability 1 Month | 12.83 | 13.07 | 12.80 | 12.91 | 12.84 |
| % Recovery after 50° C. Stability | 91.0 | 93.0 | 91.0 | 92.0 | 91.0 |

TABLE 3-continued

Chemical Stability Results of the
Preferred Aqueous Liquid Systems of the Invention

| Formulation | A 5503-109-1 | B 5503-109-2 | C 5503-111-1 | D 5503-111-2 | E 5503-111-3 |
|---|---|---|---|---|---|
| %IPBC (criterion for IPBC is 90% recovery) | | | | | |
| Initial | 2.41 | 2.32 | 2.34 | 2.28 | 2.46 |
| 40° C. Stability 1 Month | 2.38 | 2.38 | 2.48 | 2.42 | 2.43 |
| 50° C. Stability 1 Month | 2.23 | 2.20 | 2.24 | 2.27 | 2.26 |
| % Recovery after 50° C. Stability | 93.0 | 95.0 | 96.0 | 99.6 | 92.0 |

The above data show that, after one month of storage, the stabilized compositions all had stabilities of over 90%. These data illustrate that butylene glycol is the preferred solvent.

In comparison to a liquid preservative system, without the added stabilizer, DMH, recovery of IPBC after four weeks storage at 45° C. was only about 60% and does not meet the criteria of the industries that use preservatives in their products.

EXAMPLE 7

The composition of the invention described in Example 1 was tested for chemical stability at elevated temperatures and in sunlight in glass and high density polyethylene containers. The compositions were analyzed for percent total formaldehyde, percent free formaldehyde, and percent IPBC after one, two, and three months.

The results are shown in the following table:

TABLE 4

| #5503-125 | Initial | 1 month glass | 1 month HDPE | 2 months glass | 2 months HDPE | 3 months glass | 3 months HDPE |
|---|---|---|---|---|---|---|---|
| % Total HCHO | 13.02 | | | | | | |
| RT | | 13.60 | 13.40 | 13.90 | 12.80 | 13.11 | 13.21 |
| 40° C. | | 13.40 | 13.60 | 13.10 | 13.10 | 12.76 | 12.87 |
| 50° C. | | 13.10 | 13.10 | — | — | — | — |
| Sunlight | | 13.60 | 13.60 | 13.50 | 13.20 | 12.95 | 13.13 |
| Lab light | | — | — | — | — | 12.93 | 13.13 |
| % Free HCHO | 0.09 | | | | | | |
| RT | | 0.05 | 0.04 | 0.04 | 0.04 | 0.02 | 0.04 |
| 40° C. | | 0.04 | 0.06 | 0.06 | 0.05 | 0.04 | 0.06 |
| 50° C. | | 0.06 | 0.05 | — | — | — | — |
| Sunlight | | 0.05 | 0.06 | 0.09 | 0.06 | 0.07 | 0.07 |
| Lab light | | — | — | — | — | 0.03 | 0.03 |
| % IPBC | 2.49 | | | | | | |
| RT | | 2.50 | 2.50 | 2.30 | 2.30 | 2.30 | 2.30 |
| 40° C. | | 2.49 | 2.45 | 2.50 | 2.50 | 2.40 | 2.40 |
| 50° C. | | 2.26 | 2.25 | — | — | — | — |
| Sunlight | | 2.46 | 2.49 | 2.30 | 2.50 | 2.30 | 2.30 |
| Lab light | | — | — | — | — | 2.30 | 2.30 |

The above data clearly show that the composition remains stable under all conditions, i.e., at room temperature, 40° C., and 50° C. and in the presence of sunlight and laboratory lighting.

We claim:

1. A stabilized iodopropynyl solution which consisting essentially of an iodopropynyl compound and a stabilizer which is (i) a hydantoin or derivative thereof represented by Formulas III, IV, or V:

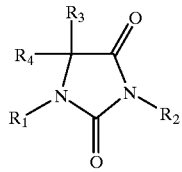

wherein $R_1$ to $R_4$ are independently selected from H, $C_1$ to $C_{22}$;

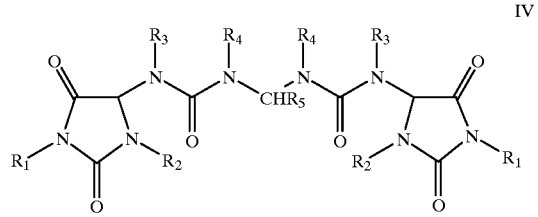

wherein $R_1$ to $R_5$ are independently selected from H or $C_1$ to $C_{22}$; or

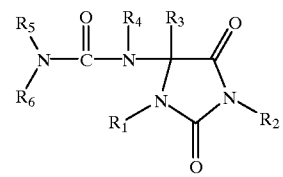

wherein $R_1$ to $R_6$ are independently selected from H, $CH_3$, $C_2H_5$ or $C_3H_7$; or (ii) urea or derivative thereof represented by Formula VI:

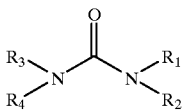

wherein $R_1$ to $R_4$ are independently selected from H or $C_1$ to $C_{12}$; the ratio of said stabilizer to iodopropynyl compound being from 150:1 to 0.05:1 and sufficient to chemically stabilize the iodopropynyl compound.

2. The solution of claim 1 wherein the stabilizer is the hydantoin or derivative thereof represented by formula III wherein $R_3$ and $R_4$ are both methyl.

3. The solution of claim 1 wherein the iodopropynyl compound is iodo-2-propynylbutyl carbamate and the stabilizer is dimethylhydantoin.

4. A liquid composition comprising an iodopropynyl compound and a stabilizer which is a hydantoin or derivative thereof represented by Formulas III, IV, or V:

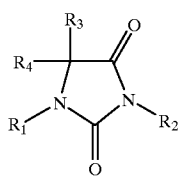

III wherein $R_1$ to $R_4$ are independently selected from H, $C_1$ to $C_{22}$;

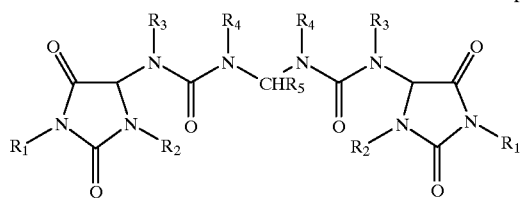

IV

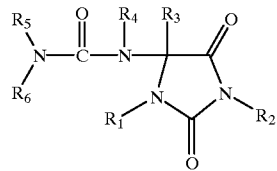

V wherein $R_1$ to $R_5$ are independently selected from H or $C_1$ to $C_{22}$; or wherein $R_1$ to $R_6$ are independently selected from H, $CH_3$, $C_2H_5$, or $C_3H_7$, the ratio of said stabilizer to iodopropynyl compound being from 150:1 to 0.05:1 and sufficient to chemically stabilize the iodopropynyl compound.

5. The composition of claim 4 wherein the stabilizer is the hydantoin or derivative thereof represented by formula III wherein $R_3$ and $R_4$ are both methyl.

6. The composition of claim 4 wherein the iodopropynyl compound is iodo-2-propynylbutyl carbamate and the stabilizer is dimethylhydantoin.

* * * * *